United States Patent [19]
Jang

[11] Patent Number: 5,843,114
[45] Date of Patent: Dec. 1, 1998

[54] SKIN PERFORATING APPARATUS FOR TRANSDERMAL MEDICATION

[75] Inventor: Kwang Kyun Jang, Kyungki-Do, Rep. of Korea

[73] Assignee: Samsung Electro-Mechanics Co., Ltd., Kyungki-do, Rep. of Korea

[21] Appl. No.: 448,236

[22] Filed: May 23, 1995

[30] Foreign Application Priority Data

May 23, 1994 [KR] Rep. of Korea ...................... 94/11250

[51] Int. Cl.⁶ .................................................. A61B 17/34
[52] U.S. Cl. .......................... 606/186; 606/183; 606/180; 606/172; 606/167; 604/46; 604/117; 604/263; 30/365
[58] Field of Search ..................................... 128/770, 753, 128/754, 762, 743; 604/22, 46, 263, 47, 115, 117, 73, 131, 134, 136, 137, 173, 181, 182, 187, 188, 192, 289, 290; 606/159–161, 167–172, 180–187; 206/363–366, 370, 380, 443, 438; 30/358, 365, 366, 367; 83/866; 600/583, 566, 567, 575, 556

[56] References Cited

U.S. PATENT DOCUMENTS

| | | | |
|---|---|---|---|
| 3,086,530 | 4/1963 | Groom | 606/186 |
| 3,208,452 | 9/1965 | Stern | 606/183 |
| 3,918,449 | 11/1975 | Pistor | 128/253 |
| 4,203,446 | 5/1980 | Höfert et al. | 606/182 |
| 4,483,348 | 11/1984 | Sher | 128/743 |
| 5,139,029 | 8/1992 | Fishman et al. | 128/743 |
| 5,224,470 | 7/1993 | Schnepp-Pesch et al. | 606/170 |
| 5,497,556 | 3/1996 | Lebessis | 30/365 |
| 5,540,709 | 7/1996 | Ramel | 606/183 |

*Primary Examiner*—Ronald Stright
*Attorney, Agent, or Firm*—Lowe Hauptman Gopstein Gilman & Berner

[57] ABSTRACT

A skin perforating member for an insulin patch, which is for disposing a human skin before administering insulin transdermally. By a pressure sensing arrangement instailed on both sides of a skin perforating member, a user can learn whether scarring a skin is properly going on at the sight of a pilot lamp. When not used, this device deposits the skin perforating member in its main body to shield perforating needles.

13 Claims, 3 Drawing Sheets

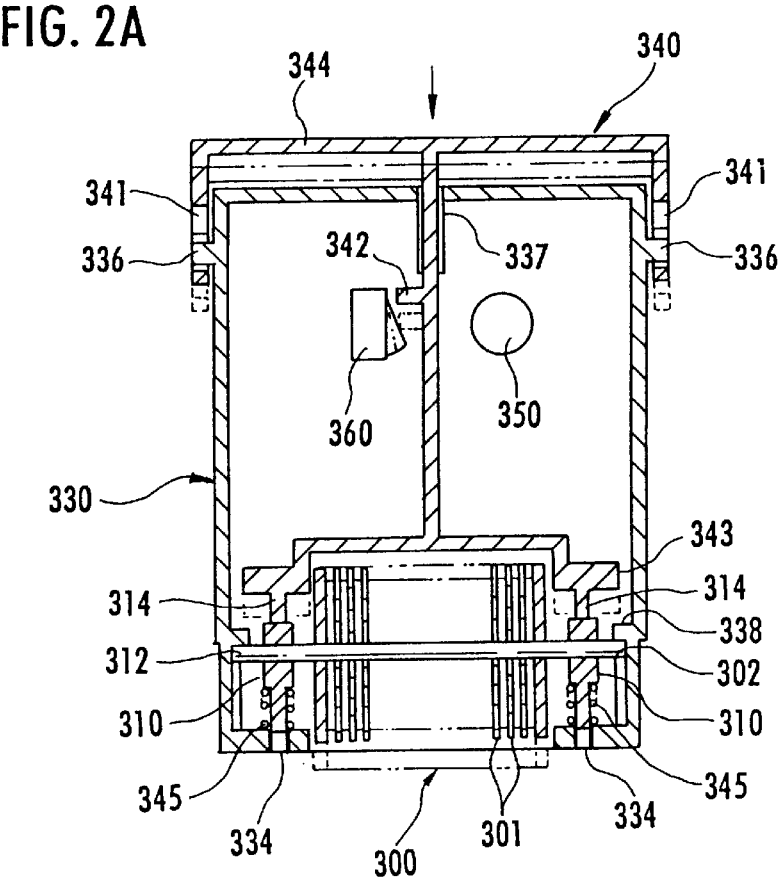
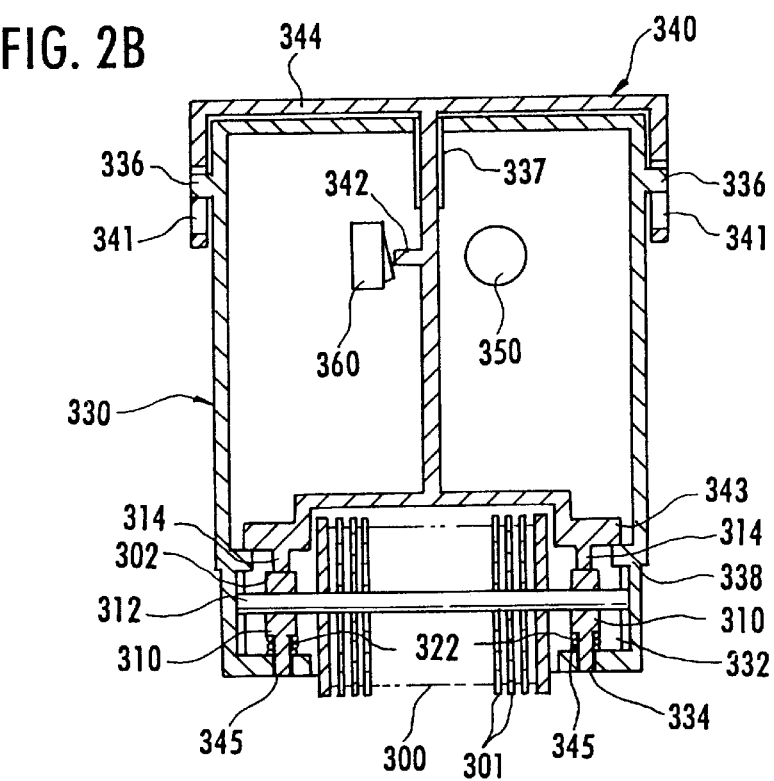

SKIN PERFORATING APPARATUS FOR TRANSDERMAL MEDICATION

FIELD OF THE INVENTION

The present invention relates to a skin perforating apparatus for transdermal medication. More specifically, this invention relates to an apparatus that perforates, when used, human skin at a regular depth under apropriate pressure. When not used, it deposits perforating needles in a main body to shield the needles.

BACKGROUND OF THE PRIOR ART

Generally, a needle plate for an insulin patch forms thousands of skin incisions within an aiming area at regular intervals. To obtain many incisions by the needle plate having a few perforating needles, a user had to move up and down and rotate the needle plate. unfortunately, however, a user could not get the uniform incisions by that manner. The incisions are concentrated densely in the middle area of the needle plate, while they are introduced more sparsely the farther away from the middle area.

To avoid such a problem, another type of device has been developed. The device employs thousands of perforating needles arranged at regular intervals in every direction on a needle plate. Without an extra assistant driver for driving the needle plate, a user could obtain thousands of skin incisions at a time by pressing the needle plate with a proper pressure.

However, in such a perforating needle plate, it was, even in an advanced technology, considerably difficult to prepare thousands of needles on a limited space. Therefore, it has had no practical use and also poor operation efficiency and inferior productivity.

Recently, a new type of apparatus has been developed. It has needle disks employing on their circumferences perforating needles. Specifically, a plurality of disks having radially perforating needles are stacked axially at regular intervals, taking turns with spacers. These disks gather to form a cylinder on which the perforating needles stand radially. Rolling the cylinder on a skin, a user can obtain the necessary number of skin incisions at a regular depth. This does not need an extra assistant driver, either, and has a low price.

However, in the conventional skin perforating apparatus for an insulin patch, exposure of perforating needles out of a main body poses the risk that the needles will be broken. Furthermore, the sight of congregated reedles may be unappealing to a user.

SUMMARY OF THE INVENTION

The present invention is developed to reflect the above facts. It is an object of this invention to provide a skin perforating apparatus for transdermal medication that deposits, when not used, perforating needles in a main body to shield the perforating needles, and presents the perforating needles only when used. Thus a user can manipulate it safely and pleasantly.

According to one feature of this invention, the present invention provides a skin perforating apparatus for transdermal medication, comprising:

a main body in which a skin perforating member having a recess portion is deposited when said appartus is not used;

a subbody, prepared on an outside of said main body, that travels by an exterior force associated with said skin perforating member through an inside of said main body;

a traveling member, joined with a bottom base of said subbody and an elastic member, as a block in said main body, that is deposited in said main body by a face of a coil spring; and skin perforating means, having a central shaft for rotation, on which a plurality of skin perforating needles are formed on a circumference of a cylinder.

According to another feature of the present invention, there is provided a skin perforating apparatus for transdermal medication, comprising:

a main body in which a skin Perforating member having a recess portion is deposited when said apparatus is not used;

a subbody, prepared on an outside of said main body, that travels by an exterior force associated with said skin perforating member through an inside of said main body;

a traveling member, contacting a bottom base of said subbody and joined with a pair of upper and lower elastic members in a block in said main body, for applying a uniform force to a skin; and skin perforating means, having a central shaft for rotation, on which a plurality of skin perforating needles are formed on a circumference of a cylinder.

Hereafter, the preferred embodiments of a skin perforating apparatus for transdermal medication according to the present invention will be described with reference to the attached drawings.

BRIEF DESCRIPTION OF THE DRAWINGS

FIGS. 2A and 2B are sectional views showing an operation situation of one embodiment of the present invention.

DESCRIPTION OF THE PREFERRED EMBODIMENTS

Figure 1:
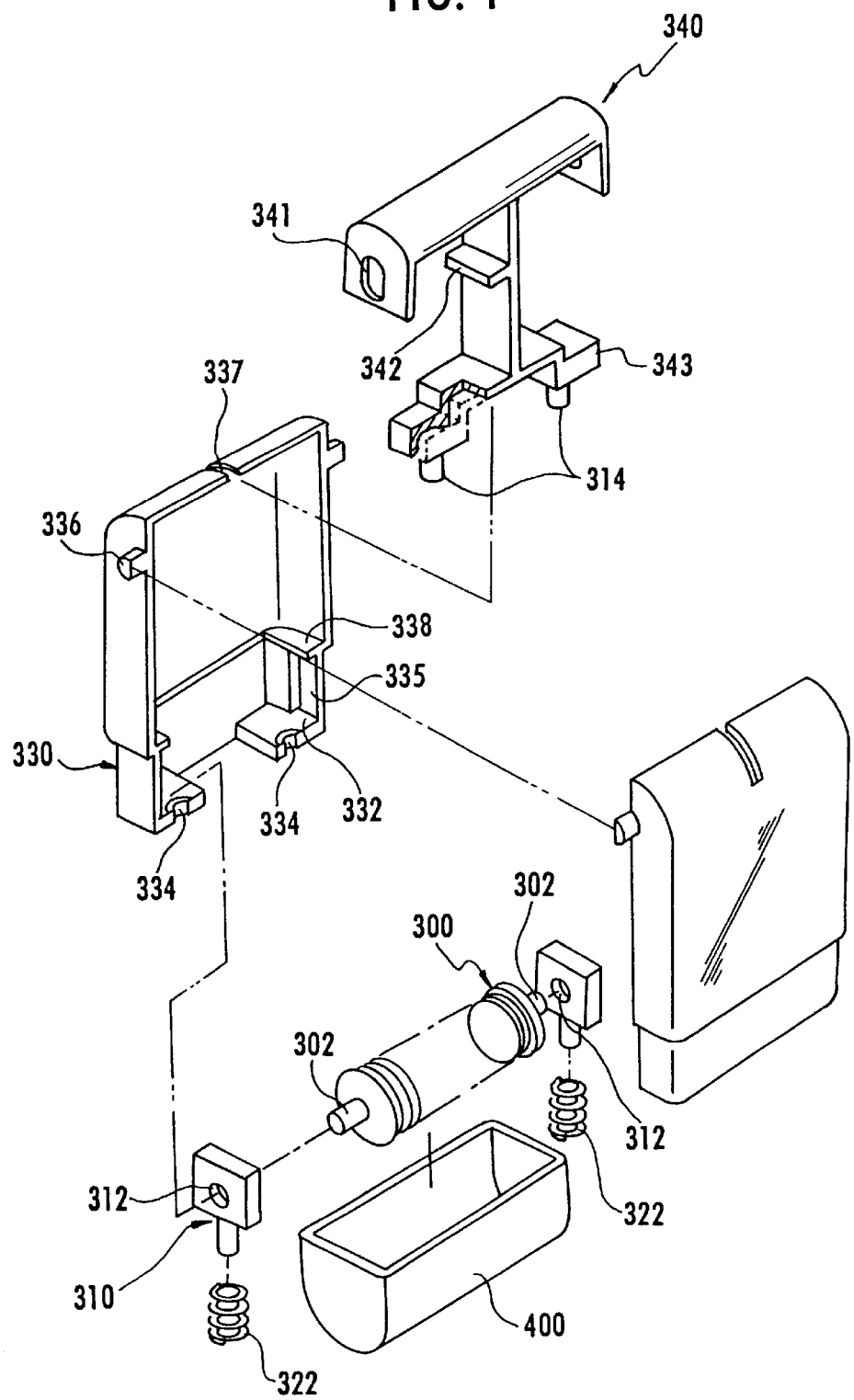
FIG. 1 is an exploded perspective view showing a skin perforating apparatus for transdermal medication according to the present invention.

As shown in FIG. 1, traveling members 310 are assembled with both sides of a shaft 302 of the skin perforating member 300. Skin perforating member 300 has a plurality of perforating needles 301 as shown in FIGS. 2A, 2B, 3A and 3B. Lower elastic members 322 are attached to the lower sides of the respective traveling members 310.

On the respective traveling members 310, a bearing 312, which is joined to the shaft 302, is formed.

The skin perforating member 300 and the traveling members 310 are equipped in a main body 330. The bottom side of the respective traveling members 310 are mounted on respective sills 332 in the bottom of the main body 330. On the respective sills 332, a through-hole 334 is introduced. Guide grooves 3035, which guide the shaft 302 to travel up and down, are prepared on both inner walls of the main body 330.

As shown in FIGS. 1 to 2B, on the outer walls of the main body 330, a first stopper 336 may be projected, which restricts the traveling range of the following subbody 340. A through-groove 337, through which the subbody 340 travels up and down, is formed on the top of the main body 330.

On the inner walls of the main body 330, besides, a second stopper 338 is formed, which restricts the traveling range of the subbody 340.

It is desirable that the main body 330 has a feature and size to such an extend that a user Can grip and apply force to easily.

The subbody 340 can travel up and down against the main body 330 when a user applies pressure.

The subbody 340 is roughly I-shaped, and forms a body with a push head 344 and a bottom base 343. Guides 314 are formed on the bottom base 343. Openings 341 that join the stopper 336 of the main body 330 are respectively formed on both sides of the push head 344. A block 342 is prepared on a central stem to prevent the subbody 340 from leaving the main body upwardly. This block 342 activates the following switch. The bottom base 343 acts to prevent the subbody 340 from going down below the second stopper 338 of the main body 330. The top of the traveling members 310 is engaged with the guides 314 of the bottom base 343.

In the upper space of the main body 330, as shown in FIG. 2, there is a light-emitting diode 350, a sensing switch 360, a battery (not illustrated) and a printed wiring board (not illustrated). A cap 400 is assembled with the bottom of the main body 330 as show in FIG. 2A.

The operation of such a constructed device in accordance with the present invention will be described.

when not in use, the lower elastic members 322 in the lower position push the traveling members 310 up. Accordingly the shaft 302 assembled to the bearing 312 ascends, and the skin perforating member 300 stands in a regular position as shown in FIG. 2A. That is, a skin perforating apparatus remains in this position ordinarily.

When in use, a user presses down the push head 344 of the subbody 340 to perforate his skin. Then the guider 314 of the bottom base 343 pushes down the upper side of the traveling members 310, and the traveling members 310 accordingly descend. At this time, the lower guides 345 of the traveling members 310 slide down through the through-holes 334 of the sill 332, and then the skin perforating member 300 descends as shown in FIG. 2B. A user now will be able to perforate his skin.

If a user releases the subbody 340 after perforating, the subbody 340 returns to its regular position by the elasticity of the elastic members 322. Therefore, the skin perforating member 300 is deposited within the main body 330 and does not protrude.

As shown in FIG. 2B, when perforating a skin, the switch 360 and the light-emitting diode 350 are turned on. A user can determine whether the perforating depth is proper by seeing the light.

Meanwhile, another embodiment of the present invention will be explained.

As shown in FIG. 3, traveling members 310 are assembled with both sides of a shaft 302 of the skin perforating member 300. Upper and lower elastic members 320 and 322 are attached to the upper and lower sides of the respective traveling members 310. Here, preferably, the elasticity of the lower elastic member 322 is stronger than that of the upper elastic member 320.

On the respective traveling members 310, a bearing 312, which is joined to the shaft 302, is formed.

The skin perforating member 300, the traveling members 310, and the elastic members 320 are equipped in a main body 330. The bottom side of the respective traveling members 310 is mounted on the respective sills 332 in the bottom of the main body 330. On the respective sills 332, a through-hole 334, through which guiders 345 of the traveling members 310 slide, is formed. The respective guide grooves 335, which guide the shaft 302 to travel up and down, are prepared on both inner walls of the main body 330.

As shown in FIGS. 1 to 2B, on the outer walls of the main body 330, a first stopper 336 may be projected, which restricts the traveling range of the following subbody 340. A through-groove 337, through which the subbody 340 travels up and down, is formed on the top of the main body 330.

On the inner walls of the main body 330, besides, a second stopper 338 is formed, which restricts the traveling range of the subbody 340.

It is preferable that the main body 330 has features and size to the extent that a user can grip and apply pressure easily.

The subbody 340 can travel up and down against the main body 330 when a user applies pressure.

The subbody 340 is roughly I-shaped, which forms in a body a push head 344 and a bottom base 343. Openings 341 that join the stopper 336 of the main body 330 are respectively formed on both sides of the push head 344. A block 342 is prepared on a central stem to prevent the subbody 340 from leaving upwardly from the main body. This block 342 activates the following switch. The bottom base 343 prevents the subbody 340 from going down below the second stopper 338 of the main body 330. This bottom base 343 is engaged with the guiders 345 of the traveling members 310 along with the upper elastic members 320.

In the upper space of the main body 330, as shown in FIG. 3, there is a light-emitting diode 350, a sensing switch 360, a battery (not illustrated) and a printed wiring board (not illustrated). A cap 400 is assembled on the bottom of the main body 330.

Figure 3A:
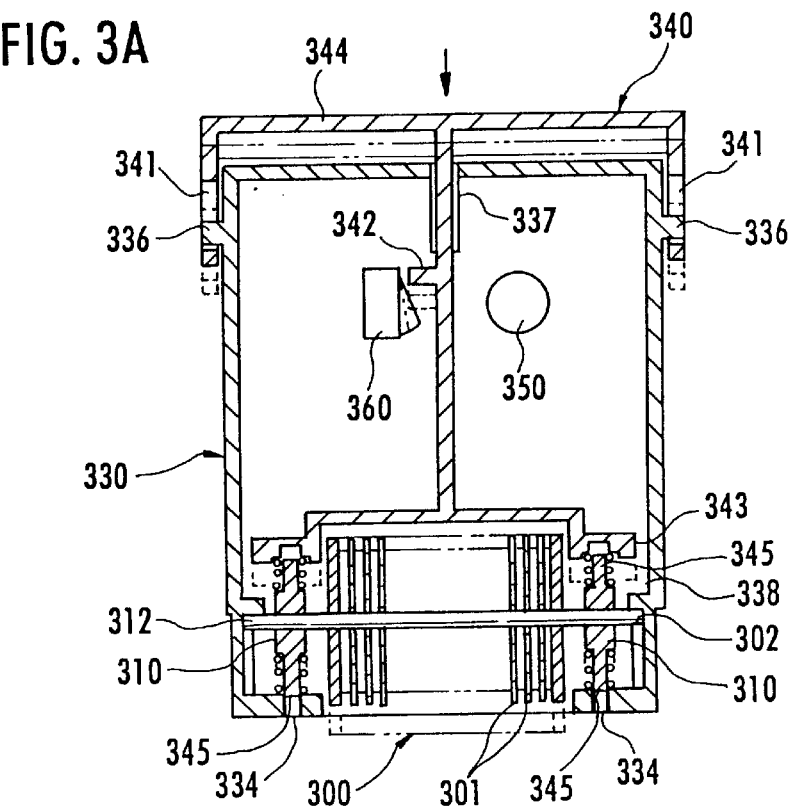
FIGS. 3A and 3B are sectional views showing an operation situation of another embodiment of the present invention.

In operation, when not used, the lower elastic members 322 in the lower position push the traveling members 310 up. Accordingly the shaft 302 in contact with the bearing 312 ascends, and the skin perforating member 300 stands in a regular position as shown in FIG. 3A. That is, a skin perforating apparatus remains in this position during nonuse.

Figure 3B:
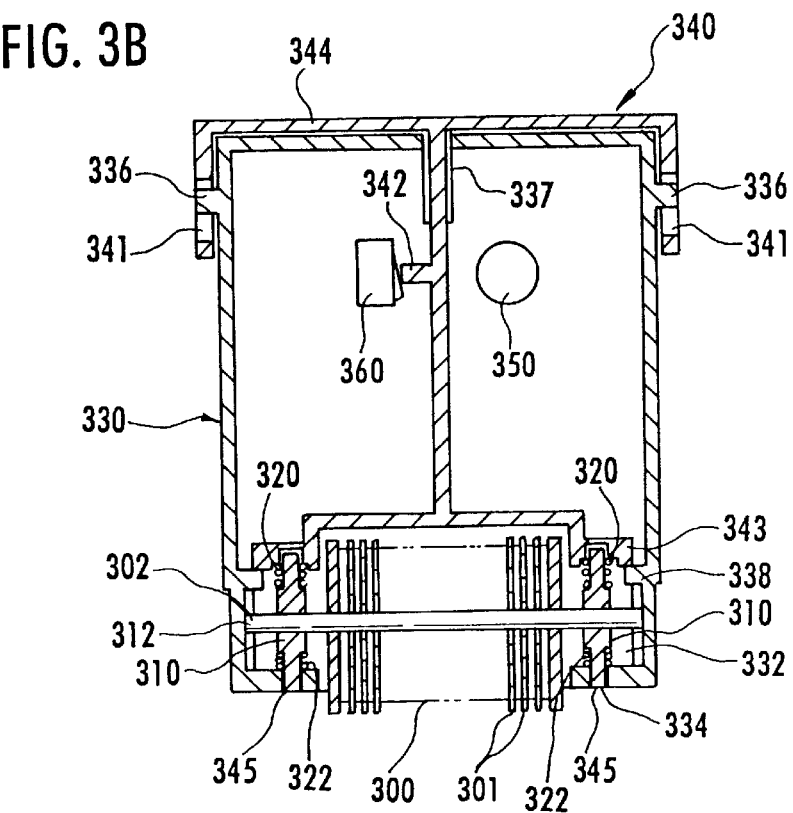

When in use, a user presses down the subbody 340 to perforate his skin. Then the bottom base 343 of the subbody 340 pushes down the upper guides 345 of the traveling members 310, and the traveling members 310 accordingly descend. At this time, the lower guides 345 slide down through the through-holes 334 of the sills 332, and the skin perforating member 300 descends as shown in FIG. 3B. A user now will be able to perforate his skin.

If a user releases the subbody 340 after perforating, the subbody 340 returns to its regular position by the elasticity of the elastic members 322. Therefore, the skin perforating member 300 is deposited in the main body 330 and does not protrude; because the elasticity of the lower elastic member 322 is stronger than that of the upper elastic member 320. It is also possible for the upper elastic member to have the same or greater elasticity than the lower elastic member.

In operation, the device is rolled along the skin to perforate the skin with the needles after the subbody 340 is pushed to cause the needles 301 to descend from the main body (see FIG. 3B) to contact the patient's skin. The rolling of the device will cause the shaft 312 and the cylinder 300 to rotate to puncture the skin with the needles.

As shown in FIG. 3B, when perforating skin, the sensing switch 360 and the light-emitting diode 350 are turned on. A user can determine whether the disposing depth is proper by sight of the light.

From the foregoing, the present invention, a skin perforating apparatus for transdermal medication, not only shields perforating needles by depositing a skin perforating member in its main body, but also provides a user with a sense of security in use.

What is claimed is:

1. A skin perforating apparatus, comprising:

a main body having a through groove formed on a top portion of said main body, stoppers protrusively formed on lower left and right portions inside said main body, sills formed on left and right lower end portions inside said main body, guide grooves formed between said stoppers and said sills, a recess portion formed inside said main body, and an apparatus for forming a plurality of punctures, said apparatus located in said recess portion when said apparatus is not in use;

a subbody being generally "I"-shaped and having an upper push head, a central stem, and a bottom base, said subbody being engaged with said main body with said through groove so that said push head is located outside of said main body and said bottom base is located within said main body;

traveling members located within said recess portion and respectively engaged with the bottom base of said subbody and said main body, and elastic members engaged with said traveling members, said traveling members thereby being located in said main body by a biasing force of said elastic members if no exterior force is applied thereto;

said elastic members biasing the traveling members to make said traveling members move elastically and vertically in the main body, said elastic members being interposed between said traveling members and the sills of said main body; and said apparatus for forming the plurality of punctures further comprising a central shaft rotatably supported by said traveling members and having a plurality of skin perforating needles formed on a circumference of the apparatus, said main body including an opening through which said needles project when said subbody is manually operated by a user depressing the push head against bias of said elastic members.

2. The apparatus according to claim 1, wherein said elastic members are coil springs.

3. The apparatus according to claim 1, wherein a traveling degree of said apparatus for forming a plurality of punctures is determined in accordance with a traveling degree of said subbody.

4. The apparatus according to claim 1, wherein said main body has a feature and size to such an extent that a user can grip and apply force to said subbody easily.

5. The apparatus according to claim 1, wherein said main body further comprises a cap which is assembled to a bottom of said main body to cover said opening.

6. A skin perforating apparatus, comprising:

a main body having a through groove formed on a top portion of said main body, stoppers protrusively formed on lower left and right portions inside said main body, sills formed on left and right lower end portions inside said main body, guide grooves formed between said stoppers and said sills, and a recess portion formed inside said main body, and an apparatus for forming a plurality of punctures, said apparatus located in said recess portion when said apparatus is not in use;

a subbody being generally "I"-shaped and having an upper push head, a central stem, and a bottom base, said subbody being engaged with said main body with said through groove so that said push head is located outside of said main body and said bottom base is located within said main body;

traveling members located within said recess portion and respectively engaged with the bottom base of said subbody and said main body, and elastic members engaged with said traveling members, said traveling members thereby being located in said main body by a biasing force of said elastic members if no exterior force is applied thereto;

said elastic members biasing the traveling members to make said traveling members move elastically and vertically in the main body, said elastic members being interposed between said traveling members and the sills of said main body; and said apparatus for forming the plurality of punctures further comprising a central shaft rotatably supported by said traveling members and having a plurality of skin perforating needles formed on a circumference of the apparatus; and means for sensing and displaying vertical movement of said subbody, said main body including an opening through which said needles project when said subbody is manually operated by a user depressing the push head against bias of said elastic members.

7. The apparatus according to claim 6, further including upper elastic members secured to upper vertically projecting side portions of each traveling member, an elasticity of said upper elastic member is equal to that of said members elastic member.

8. The apparatus according to claim 6, further including upper elastic members secured to upper vertically projecting side portions of each traveling member, an elasticity of said upper elastic members are different from that of said members elastic member.

9. The apparatus according to claim 6, further including upper elastic members secured to upper vertically projecting side portions of each traveling member, an elasticity of said elastic members are stronger than that of said upper elastic members.

10. The apparatus according to claim 6, upper elastic members secured to upper vertically projecting side portions of each traveling member, said upper and elastic members are coil springs.

11. The apparatus according to claim 6, wherein a traveling degree of said apparatus for forming a plurality of punctures is determined in accordance with a traveling degree of said subbody.

12. The apparatus according to claim 6, wherein said main body has a feature a size to such an extent that a user can grip and apply force to said subbody easily.

13. The apparatus according to claim 6, wherein said main body further comprises a cap which is assembled to a bottom of said main body to cover said opening.

* * * * *